(12) United States Patent
Wei et al.

(10) Patent No.: US 11,814,405 B2
(45) Date of Patent: Nov. 14, 2023

(54) PYRIDINE SULFONAMIDE PHOSPHATE COMPOUND, PREPARATION METHOD THEREFOR, AND USE THEREOF

(71) Applicant: Shanghai Xunhe Pharmaceutical Technology Co. Ltd., Shanghai (CN)

(72) Inventors: Nongnong Wei, Shanghai (CN); Hua Jin, Shanghai (CN); Yongyong Zheng, Shanghai (CN); Feng Zhou, Shanghai (CN); Meihua Huang, Shanghai (CN)

(73) Assignee: Shanghai Xunhe Pharmaceutical Technology Co. Ltd., Shanghai (CN)

( * ) Notice: Subject to any disclaimer, the term of this patent is extended or adjusted under 35 U.S.C. 154(b) by 27 days.

(21) Appl. No.: 17/675,681

(22) Filed: Feb. 18, 2022

(65) Prior Publication Data
US 2022/0169666 A1    Jun. 2, 2022

Related U.S. Application Data

(63) Continuation of application No. PCT/CN2020/094379, filed on Jun. 4, 2020.

(30) Foreign Application Priority Data

Sep. 29, 2019    (CN) .......................... 201910930296.X

(51) Int. Cl.
*C07F 9/09*    (2006.01)
(52) U.S. Cl.
CPC .................................... *C07F 9/09* (2013.01)

(58) Field of Classification Search
CPC ........................................................ C07F 9/09
USPC .......................................................... 514/89
See application file for complete search history.

(56) References Cited

FOREIGN PATENT DOCUMENTS

| CN | 104341451 A | 2/2015 |
|---|---|---|
| CN | 110054647 A | 7/2019 |
| CN | 110606860 A | 12/2019 |
| EP | 0151451 A1 | 8/1985 |

OTHER PUBLICATIONS

International Search Report, Application No. PCT/CN2020/094379, dated Aug. 11, 2020, 3 pages.
Yujian et al., Prodrugs: Design and Clinical Application, Journal of International Pharmaceutical Research, vol. 35, No. 5, p. 378, Figure 2, Oct. 31, 2008, 1 page.

*Primary Examiner* — Kristin A Vajda
(74) *Attorney, Agent, or Firm* — ZIEGLER IP LAW GROUP LLC

(57) ABSTRACT

The present invention relates to the technical field of biomedicine, particularly to a pyridine sulfonamide phosphate compound, a preparation method therefor, and a use thereof. The invention provides the following technical benefits: the pyridine sulfonamide phosphate compound has characteristics of high solubility, high stability, ease of being made into preparations, etc., which is easy to be industrially scaled up for medical use.

8 Claims, No Drawings

PYRIDINE SULFONAMIDE PHOSPHATE COMPOUND, PREPARATION METHOD THEREFOR, AND USE THEREOF

CROSS-REFERENCE TO RELATED APPLICATIONS

The present application is a continuation application of PCT application No. PCT/CN2020/094379, filed on Jun. 4, 2020, which is hereby incorporated by reference in its entirety.

TECHNICAL FIELD

The present invention relates to the technical field of biomedicine, particularly to a pyridine sulfonamide phosphate compound, preparation method therefor, and use thereof.

BACKGROUND ART

Torsemide, namely 1-[4-(3-methylphenyl)aminopyridin-3-yl]sulfonyl-3-isopropylurea, is a new generation of highly effective loop diuretic. Torsemide has a pKa value of 6.44. It is almost insoluble in water and slightly soluble in 0.1 mol/L sodium hydroxide solution. More than 20 years of clinical applications have confirmed that torsemide has a wide range of indications and a rapid, powerful and long-lasting diuretic effect, which is a class of highly effective diuretic worthy of promotion in clinical practice.

At present, the dosage forms of torsemide on the market are injections, tablets, and capsules. In the process of preparing injections, it is desired that the bulk drug has high water solubility. Torsemide is very slightly soluble in water (European Journal of Pharmaceutics and Biopharmaceutics 53 (2002) 75-86). When preparing the injection form of torsemide, sodium hydroxide and a large amount of excipients need to be added to aid dissolution, including polyethylene glycol 400, tromethamine, sodium hydroxide, hydrochloric acid, etc. The addition of the above-mentioned excipients brings many disadvantages as follows: 1) the process of dissolving torsemide with sodium hydroxide solution is significantly exothermic, which is easy to produce impurities resulting from the degradation of the preparation; and 2) the addition of organic co-solvents such as polyethylene glycol 400, tromethamine, etc. brings hidden dangers to the safety of injections. It is desirable to reduce the types of ingredients in the formulation in order to reduce potential side effects to patients. Therefore, it is a great challenge to develop a new type of loop diuretic with higher water solubility and easier preparation.

The prior art (Drugs 41 (1): 81-103, 1991) reported an active metabolite M3 of torsemide in vivo, which has a pharmacological activity comparable to torsemide. Compared with torsemide, a phenolic hydroxyl is introduced onto the benzene ring in M3. However, the water solubility of M3 has not been effectively improved, and the preparation of the formulations remains difficult. Therefore, the inventors intended to make further modifications on the basis of M3 to obtain a drug with good water solubility while maintaining a good diuretic effect.

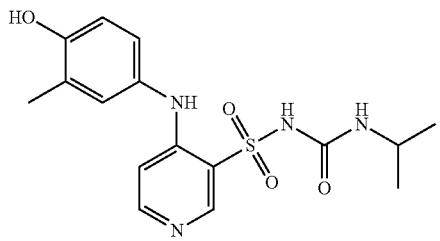

M3

SUMMARY OF THE INVENTION

The objective of the present invention is to provide a pyridine sulfonamide phosphate compound of formula I or a pharmaceutical salt thereof:

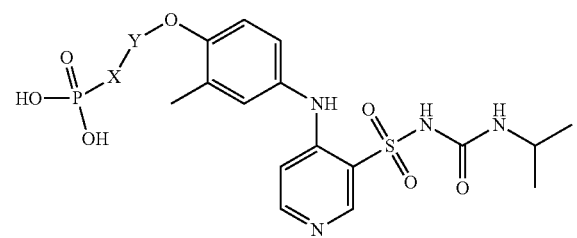

I wherein X is O or C, or does not exist; and Y is C, or does not exist. When X and Y do not exist, O is directly connected to P. When X exists but Y does not exist, X is directly connected to O. When Y exists but X does not exist, Y is directly connected to P.

Preferably, the pharmaceutical salt may include metal salt, salt formed with inorganic base, salt formed with organic base, salt formed with basic amino acid, etc. The examples of the metal salt include, but are not limited to, alkali metal salt such as sodium salt, potassium salt, etc.; and alkaline earth metal salt such as calcium salt, magnesium salt, barium salt, aluminum salt, etc. The examples of the organic base include, but are not limited to, trimethylamine, triethylamine, tripropylamine, tributylamine, or diisopropylethylamine.

Preferably, the pyridine sulfonamide phosphate compound or pharmaceutical salt thereof is selected from the following compounds:

TABLE 1

| Compound | Structural formula |
|---|---|
| I-1 | |

TABLE 1-continued

| Compound | Structural formula |
|---|---|
| I-2 | (structure: 4-(dipotassium phosphate)-3-methylphenyl linked via NH to pyridine-sulfonyl-urea-isopropyl) |
| I-3 | (structure: 4-(phosphonic acid)-3-methylphenyl linked via NH to pyridine-sulfonyl-urea-isopropyl, with triethylamine counterion) |
| I-4 | (structure: 4-(phosphonic acid)-3-methylphenyl linked via NH to pyridine-sulfonyl-urea-isopropyl, with tributylamine counterion) |
| II-1 | (structure: 4-(disodium phosphoryloxymethoxy)-3-methylphenyl linked via NH to pyridine-sulfonyl-urea-isopropyl) |
| II-2 | (structure: 4-(dipotassium phosphoryloxymethoxy)-3-methylphenyl linked via NH to pyridine-sulfonyl-urea-isopropyl) |

TABLE 1-continued

| Compound | Structural formula |
|---|---|
| III-1 | 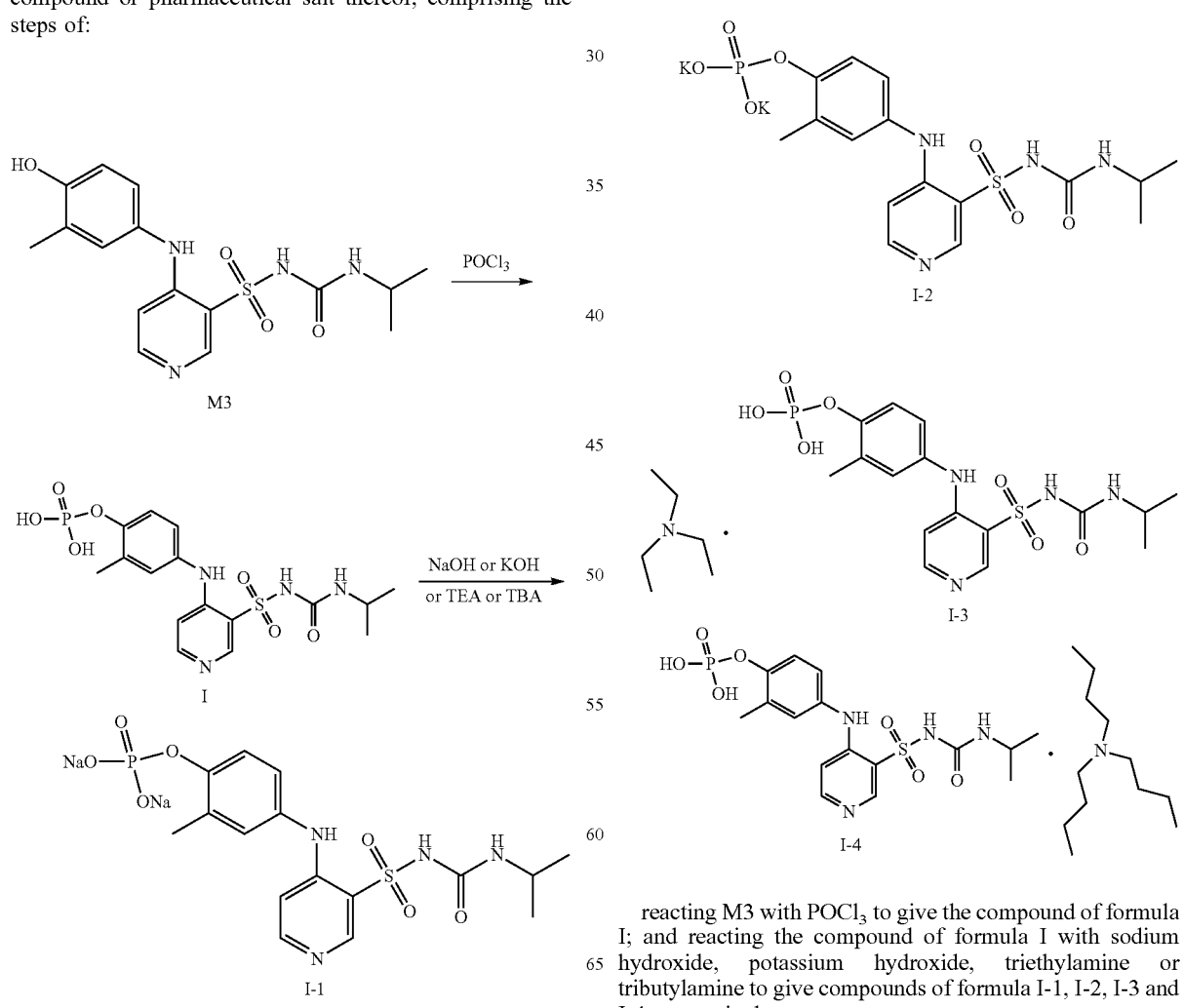 |
| III-2 | |

In the second aspect, the present invention provides a method for preparing the pyridine sulfonamide phosphate compound or pharmaceutical salt thereof, comprising the steps of:

reacting M3 with $POCl_3$ to give the compound of formula I; and reacting the compound of formula I with sodium hydroxide, potassium hydroxide, triethylamine or tributylamine to give compounds of formula I-1, I-2, I-3 and I-4, respectively.

Or, the method comprises the steps of:

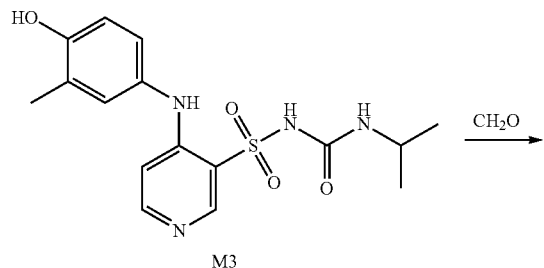

M3

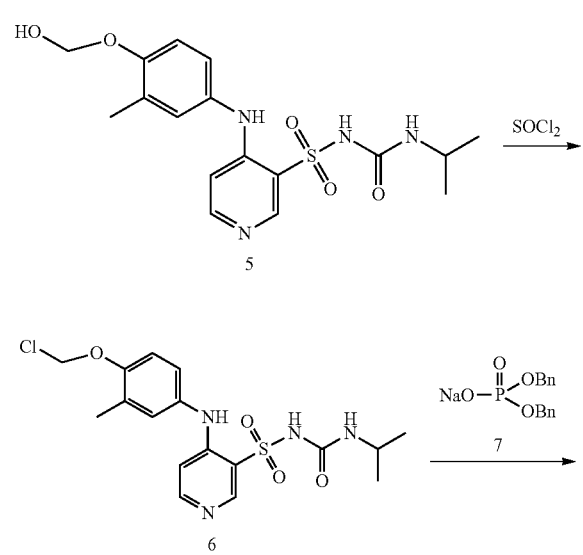

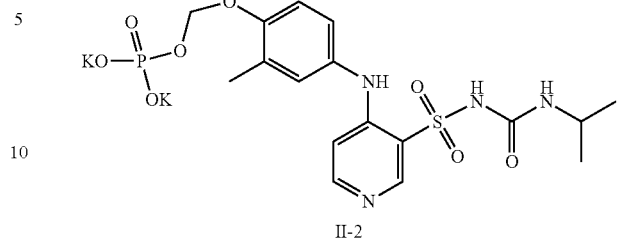

II-2 subjecting M3 to hydroxymethylation with paraformaldehyde, chlorination, esterification, and debenzylation via hydrogenation to give a compound of formula II; and reacting the compound of formula II with sodium hydroxide and potassium hydroxide to give compounds of formula II-1 and II-2, respectively.

Or, the method comprises the steps of:

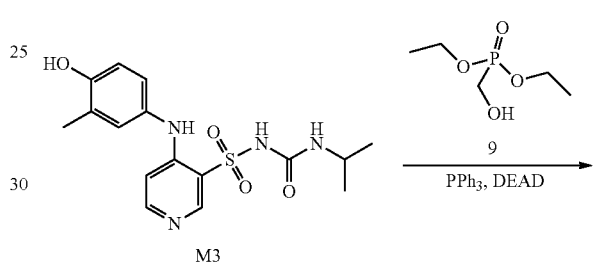

M3

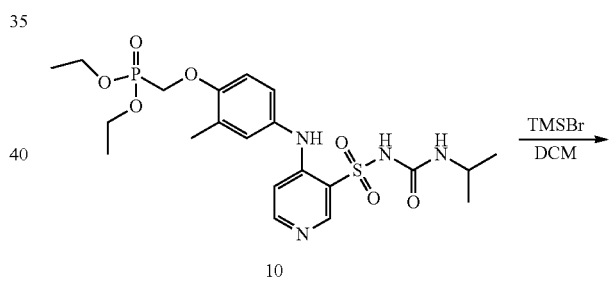

10

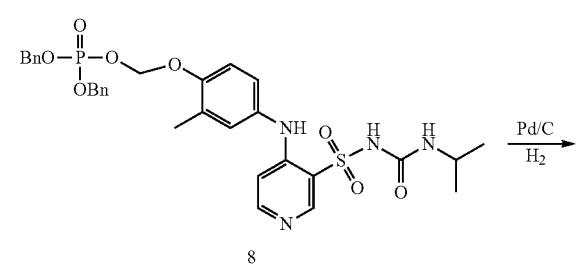

II

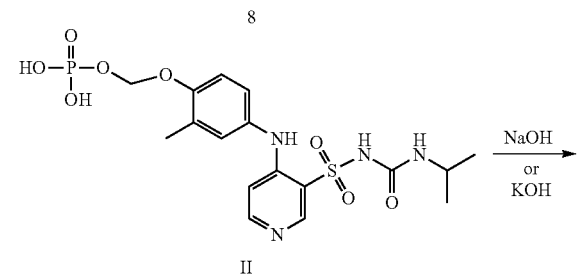

II-1

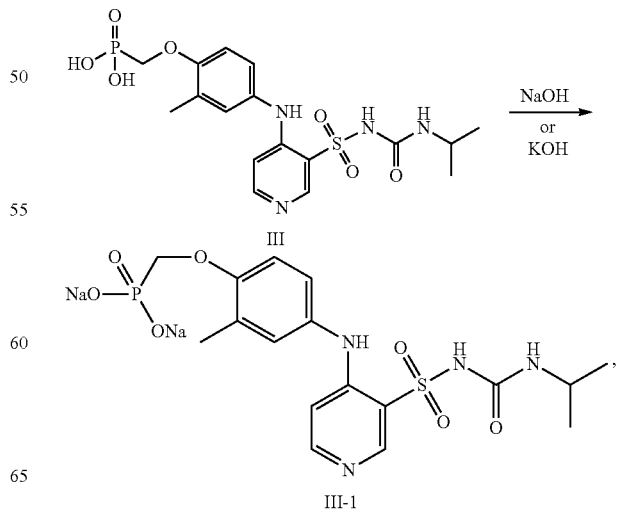

III

III-1

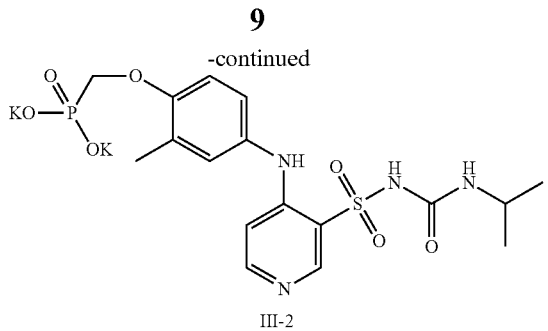

III-2 subjecting M3 to reaction with diethyl hydroxymethyl phosphonate (9), and then to deethylation to give a compound of formula III; and reacting the compound of formula III with sodium hydroxide and potassium hydroxide to give compounds of formula III-1 and III-2, respectively.

In the third aspect, the present invention provides a pharmaceutical composition, comprising a therapeutically effective amount of the pyridine sulfonamide phosphate compound or pharmaceutical salt thereof and a pharmaceutically acceptable excipient.

The excipient mentioned above refer to excipient commonly used in the pharmaceutical field, for example, diluents, excipients such as water; binders such as cellulose derivatives, gelatin, polyvinylpyrrolidone, etc.; fillers such as starch, etc.; and disintegrating agents such as calcium carbonate and sodium bicarbonate. In addition, other auxiliary agents such as flavoring agents and sweetening agents may also be added to the composition.

Various dosage forms of the composition of the present invention can be prepared by conventional methods in the medical field, wherein the content of the active ingredient is 0.1% to 99.5 wt %.

The dosage of the composition of the present invention may vary depending on the route of administration, the age and weight of the patient, the type and severity of the disease to be treated, and the like. The daily dose is 0.001 to 30 mg/kg body weight for oral administration or 0.005 to 30 mg/kg body weight for injection.

In the fourth aspect, the present invention provides the use of the pyridine sulfonamide phosphate compound or pharmaceutical salt thereof in the preparation of diuretics.

The invention has the following technical benefits: the pyridine sulfonamide phosphate compound has characteristics of high solubility, high stability, ease of being made into preparations, etc., which is easy to be industrially scaled up for medical use.

DETAILED DESCRIPTION

In the following, the present invention will be further described in detail with reference to the embodiments, but it is not limited thereto.

EXAMPLE 1

Preparation of Compound of Formula I

Step 1: Preparation of Compound of Formula 3

Anhydrous ethanol (300 mL) and compound 2 (18.5 g, 0.15 mol, 1.05 eq) were added to a 500 mL reaction flask, stirred and heated to about 75° C. Compound 1 (27.5 g, 0.143 mol, 1.0 eq) was added in batches. After the addition, the reaction continued at this temperature for 1 h while stirring, and a solid precipitated. The mixture was cooled to 20-25° C., sodium carbonate (15.9 g, 0.15 mol, 1.5 eq) was added, and paraformaldehyde (15 g, 0.5 mol, 5 eq) was added in batches while stirring. After the addition, the mixture was heated to 80-85° C. to react for 2 h, then slowly cooled to 20-25° C., filtered and drained to obtain a faint yellow filter cake as the compound of formula 3 (36.5 g, yield 81%), MS: 280 [M+1].

Step 2: Preparation of Compound of Formula M3

Acetone (200 mL), compound of formula 3 (35 g, 0.11 mol, 1.0 eq) and sodium hydroxide (8.87 g, 0.22 mol, 2.0 eq) were added to a 500 mL reaction flask. Compound 4 (11.2 g, 0.13 mol, 1.2 eq) was added dropwise at 20-25° C. After the dropwise addition, the mixture was heated to 45-50° C. and stirred for 1 h to complete the reaction, cooled to 8-12° C. and maintained for another 1 h, filtered and drained to obtain an off-white wet product. The wet product was added to purified water (200 mL) and 6% acetic acid aqueous solution was added dropwise to adjust the pH to 6-7 (pH test paper) at 20-25° C. The mixture was stirred for half an hour and filtered. The filter cake was washed with purified water and drained to obtain a wet product of M3. The wet product was vacuum dried to a constant weight at 55-60° C. to obtain compound M3 (34 g, yield 85%), MS: 365 [M+1].

Step 3: Preparation of Compound of Formula I

Tetrahydrofuran (150 mL), compound M3 (15 g, 41.2 mmol, 1.0 eq) and diisopropylethylamine (5.3 g, 41.2 mmol, 1.0 eq) were added into a 250 mL reaction flask. The mixture was cooled to 0-5° C., and phosphorus oxychloride (6.3 g, 41.2 mml, 1.0 eq) was added dropwise while stirring. After the addition, the mixture reacted at 0-5° C. for 2 h. This temperature was maintained and water (5 mL) was added to quench the reaction. The solvent was concentrated to dryness to obtain a concentrated residue. The residue was passed through a neutral alumina column (eluent: dichloromethane/methanol 10:1). The obtained fraction was concentrated and dried under vacuum at 40-45° C. to a constant weight to obtain compound I (11.9 g, yield 65%), MS: 445 [M+1]. $^1$H NMR (400 MHz, D$_2$O) δ: 8.66 (s, 1 H), 8.05-8.06 (d, J=5.2 Hz, 1 H), 7.29 (m, 1 H), 7.21-7.22 (d, J=5.2 Hz, 1 H), 6.88 (m, 1 H), 6.58 (s, 1 H), 4.27 (m, 1 H), 2.27 (s, 3 H), 0.95 (s, 3 H), 0.94 (s, 3 H).

EXAMPLE 2

Preparation of Compound of Formula I-1

Anhydrous ethanol (20 mL) and the compound of formula I (2.5 g, 5.6 mmol, 1.0 eq) were added to a 50 mL reaction flask, and 25% sodium hydroxide solution (0.45 g, 11.3 mmol, 2.0 eq) was added dropwise while stirring. After the addition, the mixture reacted for 1 h while stirring. Acetone (20 mL) was added to the reaction solution. The stirring continued for 30 min. The mixture was filtered to obtain the crude disodium salt. The obtained crude product was recrystallized by being added to acetone (20 mL)/H$_2$O (2 mL) system, and then filtered. The filter cake was vacuum dried (50° C.) to obtain the compound of formula I-1 (1.8 g, yield 65%), with a purity of 99.25% by HPLC. MS: 489 [M+1], $^1$H NMR (400 MHz, D$_2$O) δ: 8.63 (s, 1 H), 8.06-8.07 (d, J=5.2 Hz, 1 H), 7.27 (m, 1 H), 7.22-7.23 (d, J=5.2 Hz, 1 H), 6.89 (m, 1 H), 6.57 (s, 1 H), 4.25 (m, 1 H), 2.25 (s, 3 H), 0.95 (s, 6 H). Sodium content: 9.45%.

EXAMPLE 3

Preparation of Compound of Formula I-2

Anhydrous ethanol (20 mL) and the compound of formula I (2.5 g, 5.6 mmol, 1.0 eq) were added to a 50 mL reaction flask, and 20% potassium hydroxide solution (0.63 g, 11.3 mmol, 2.0 eq) was added dropwise while stirring. After the addition, the mixture reacted for 1 h while stirring. Acetone (20 mL) was added to the reaction solution. The stirring continued for 30 min. The mixture was filtered to obtain the crude dipotassium salt. The obtained crude product was recrystallized by being added to acetone (20 mL)/H$_2$O (2 mL) system, and then filtered. The filter cake was vacuum dried (50° C.) to obtain the compound of formula I-2 (1.7 g, yield 59%), with a purity of 99.05% by HPLC. MS: 521 [M+1], $^1$NMR (400 MHz, D$_2$O) δ: 8.65 (s, 1 H), 8.07 (m, 1 H), 7.22-7.26 (m, 2 H), 6.88 (m, 1 H), 6.56 (s, 1 H), 4.27 (m, 1 H), 2.26 (s, 3 H), 0.94 (s, 6 H). Potassium content: 15.00%.

EXAMPLE 4

Preparation of Compound of Formula I-3

Anhydrous ethanol (20 mL), the compound of formula I (2.5 g, 5.6 mmol, 1.0 eq) and triethylamine (0.57 g, 5.6 mmol, 1.0 eq) were added to a 50 mL reaction flask, and reacted for 1 h while stirring. The mixture was concentrated to dryness to obtain a foamy solid, which was recrystallized with acetone (10 mL) and filtered. The filter cake was vacuum dried (40° C.) to obtain the compound of formula I-3 (1.7 g, yield 56%), with a purity of 98.60% by HPLC. MS: 445 [M+1], $^1$NMR (400 MHz, D$_2$O) δ: 8.56 (s, 1 H), 7.97 (d, J=4.0 Hz, 1 H), 7.25 (m, 2 H), 6.87 (m, 1 H), 6.61 (s, 1 H), 4.28 (m, 1 H), 3.08 (m, 6 H), 2.27 (s, 3 H), 1.09 (m, 9 H), 0.94 (s, 6 H).

EXAMPLE 5

Preparation of Compound of Formula I-4

Anhydrous ethanol (20 mL), compound of formula I (2.5 g, 5.6 mmol, 1.0 eq), and tributylamine (1.04 g, 5.6 mmol, 1.0 eq) were added to a 50 mL reaction flask, and reacted for 1 h while stirring. The mixture was concentrated to dryness to obtain a foamy solid, which was recrystallized with acetone (10 mL) and filtered. The filter cake was vacuum dried (40° C.) to obtain the compound of formula I-4 (1.8 g, yield 51%), with an purity of 98.75% by HPLC. MS: 445 [M+1], $^1$ NMR (400 MHz, D$_2$O) δ: 8.59 (s, 1 H), 7.98 (d, J=4.0 Hz, 1 H), 7.27 (m, 2 H), 6.88 (m, 1 H), 6.65 (s, 1 H), 4.21 (m, 1 H), 3.05 (m, 6 H), 2.23 (s, 3 H), 1.35-1.42 (m, 12 H), 0.93 (s, 6 H), 0.87 (m, 9 H).

EXAMPLE 6

Preparation of Compound of Formula II

Step 1: Preparation of Compound of Formula 5

Anhydrous ethanol (300 mL), compound M3 (15 g, 41.2 mmol, 1.0 eq) and sodium carbonate (6.5 g, 61.7 mmol, 1.5 eq) were added into a 500 mL reaction flask, and paraformaldehyde (6.2 g, 0.21 mol, 5.0 eq) was added in batches while stirring. After the addition, the mixture was heated to 80-85° C. to react for 2 h, then slowly cooled to 20-25° C., and a white solid precipitated, filtered and washed with water. The filter cake was vacuum dried (40° C.) to obtain the compound of formula 5 (12.8 g, yield 79%), MS: 395 [M+1].

Step 2: Preparation of Compound of Formula 6

Dichloromethane (100 mL), N, N-dimethylformamide (2 mL) and compound 5 (12 g, 30.4 mmol, 1.0 eq) were added to a 250 mL reaction flask, and thionyl chloride (10.9 g, 91.3 mmol, 3.0 eq) was added dropwise while stirring. After the addition, the mixture was heated to 60-65° C. to react for 2 h. After the reaction, the solution was poured into a 500 mL beaker, and 10% sodium carbonate aqueous solution (50 mL) was added dropwise in batches under ice bath. The liquid was separated with a separating funnel. The water phase was removed. The organic phase was washed twice with water (50 mL×2) and once with saturated brine (50 mL). The mixture was separated, dried over anhydrous sodium sulfate, and concentrated to dryness. The residue was beating washed with ethyl acetate (50 mL) and filtered. The filter cake was vacuum dried (40° C.) to obtain the compound of formula 6 (10.7 g, yield 85%), MS: 413 [M+1].

Step 3: Preparation of Compound of Formula 8

Acetonitrile (100 mL), compound 6 (10 g, 24.2 mmol, 1.0 eq), sodium carbonate (5.1 g, 48.4 mmol, 2.0 eq) and dibenzyl phosphate sodium salt 7 (8.0 g, 26.6 mmol, 1.1 eq) were added to a 250 mL reaction flask. The mixture was heated to 80-85° C. to react for 8 h while stirring, and filtered to remove the inorganic salts while it is hot. The filtrate was concentrated to dryness. The concentrated residue was recrystallized with toluene (50 mL) and filtered. The filter cake was vacuum dried (50° C.) to obtain the compound of formula 8 (7.1 g, yield 45%), MS: 655 [M+1].

Step 4: Preparation of Compound of Formula II

Anhydrous ethanol (400 mL), compound 8 (7 g, 10.7 mmol, 1.0 eq) and 10% palladium on carbon (0.7 g, 10 wt %) were added to the autoclave. The gas in the autoclave was replaced with nitrogen three times, and hydrogen was introduced to get a pressure of 2 MPa. The mixture reacted at room temperature for 5 h while stirring. After the reaction was complete, the mixture was filtered. The filtrate was concentrated to dryness to obtain a white solid compound of formula II (4.1 g, yield 81%), MS: 475 [M+1]. $^1$H NMR (400 MHz, D$_2$O) δ: 8.65 (s, 1 H), 7.99 (d, J=4.0 Hz, 1 H), 7.24 (m, 2 H), 6.91 (m, 1 H), 6.59 (s, 1 H), 5.93 (s, 2 H), 4.25 (m, 1 H), 2.25 (s, 3 H), 0.95 (s, 6 H).

EXAMPLE 7

Preparation of Compound of Formula II-1

Anhydrous ethanol (20 mL) and the compound of formula II (2 g, 4.2 mmol, 1.0 eq) were added to a 50 mL reaction flask. 25% sodium hydroxide solution (0.34 g, 8.4 mmol, 2.0 eq) was added dropwise while stirring. After the addition, the mixture reacted for 1 h while stirring. Acetone (10 mL) was added to the reaction solution. The stirring continued for 30 min. The mixture was filtered to obtain the crude disodium salt. The obtained crude product was recrystallized by being added to acetone (10 mL)/H$_2$O (1 mL) system and filtered. The filter cake was vacuum dried (50° C.) to obtain the compound of formula II-1 (1.3 g, yield 60%), with a purity of 98.75% by HPLC. MS: 519 [M+1], $^1$ NMR (400 MHz, D$_2$O) δ: 8.64 (s, 1 H), 8.07-8.08 (d, J=5.2 Hz, 1 H), 7.25 (m, 2 H), 6.89 (m, 1 H), 6.59 (s, 1 H), 5.94 (s, 2 H), 4.27 (m, 1 H), 2.27 (s, 3 H), 0.94 (s, 6 H). Sodium content: 8.85%.

EXAMPLE 8

Preparation of Compound of Formula II-2

Anhydrous ethanol (20 mL) and the compound of formula I (2 g, 4.2 mmol, 1.0 eq) were added to a 50 mL reaction flask. 20% potassium hydroxide solution (0.47 g, 8.4 mmol, 2.0 eq) was added dropwise while stirring. After the addition, the mixture reacted for 1 h while stirring. Acetone (10 mL) was added to the reaction solution. The stirring continued for 30 min. The mixture was filtered to obtain the crude dipotassium salt. The obtained crude product was recrystallized by being added to acetone (10 mL)/H$_2$O (1 mL) system and filtered. The filter cake was vacuum dried (50° C.) to obtain the compound of formula II-2 (1.3 g, yield 56%), with a purity of 99.15% by HPLC. MS: 551 [M+1], $^1$ NMR (400 MHz, D$_2$O) δ: 8.63 (s, 1 H), 8.07 (d, J=5.2 Hz, 1 H), 7.26 (m, 2 H), 6.92 (m, 1 H), 6.61 (s, 1 H), 5.93 (s, 2 H), 4.25 (m, 1 H), 2.25 (s, 3 H), 0.95 (s, 6 H). Potassium content: 14.21%.

EXAMPLE 9

Preparation of Compound of Formula III

Step 1: Preparation of Compound of Formula 10

Anhydrous tetrahydrofuran (200 mL), compound M3 (15 g, 41.2 mmol, 1.0 eq), compound 9 (6.9 g, 41.2 mmol, 1.0 eq), PPh$_3$ (1.6 g, 6.2 mmol, 0.15 eq) and DEAD (1 g, 6.2 mmol, 0.15 eq) were added into a 500 mL reaction flask. The mixture reacted at 30-35° C. for 24 hours while stirring. The reaction solution was concentrated to dryness. The residue was purified by silica gel column chromatography (mobile phase: dichloromethane) to obtain the compound of formula 10 (13.8 g, yield 65%), MS: 515 [M+1].

Step 2: Preparation of Compound of Formula III

Dichloromethane (100 mL) and compound 10 (12 g, 23.3 mmol, 1.0 eq) were added to a 250 mL reaction flask, cooled to 0-5° C. while stirring and TMSBr (3.6 g, 23.3 mmol, 1.0 eq) was added dropwise. The mixture reacted for 24 hours at 20-25° C. while stirring. The reaction solution was concentrated to dryness. The residue was purified by silica gel column chromatography (methylene chloride/methanol=10:1 in the mobile phase) to obtain the compound of formula III (6.2 g, yield 58%), MS: 459 [M+1].

EXAMPLE 10

Preparation of Compound of Formula III-1

Anhydrous ethanol (20 mL) and the compound of formula III (3 g, 6.5 mmol, 1.0 eq) were added to a 50 mL reaction flask. 25% sodium hydroxide solution (0.52 g, 13.1 mmol, 2.0 eq) was added dropwise while stirring. After the addition, the mixture reacted for 1 h while stirring. Acetone (10 mL) was added to the reaction solution. The stirring continued for 30 minutes. The mixture was filtered to obtain the crude disodium salt. The obtained crude product was recrystallized by being added to acetone (10 mL)/H$_2$O (1 mL) system and filtered. The filter cake was vacuum dried (50° C.) to obtain the compound of formula III-1 (2.2 g, yield 68%), with an purity of 98.95% by HPLC. MS: 503 [M+1]. Sodium content: 9.13%.

EXAMPLE 11

Preparation of Compound of Formula III-2

Anhydrous ethanol (20 mL) and the compound of formula III (3 g, 6.5 mmol, 1.0 eq) were added to a 50 mL reaction flask. 20% potassium hydroxide solution (0.73 g, 13.1 mmol, 2.0 eq) was added dropwise while stirring. After the addition, the mixture reacted for 1 h while stirring. Acetone (10 mL) was added to the reaction solution. The stirring continued for 30 minutes. The mixture was filtered to obtain the crude dipotassium salt. The obtained crude product was recrystallized by being added to acetone (10 mL)/H$_2$O (1 mL) system and filtered. The filter cake was vacuum dried (50° C.) to obtain the compound of formula III-2 (2.3 g, yield 66%), with an purity of 99.19% by HPLC. MS: 535 [M+1]. Potassium content: 14.65%.

EXAMPLE 12

Preparation of Injection of Compound of Formula I-1

The composition of the preparation: 10 g of the compound of formula I-1 and 2000 mL of water for injection.

Preparation Process (1) 10 g of the compound of formula I-1 was added to 2000 mL of water for injection. The mixture was stirred uniformly, and pre-filtered through a plate-and-frame filter to obtain solution A;

(2) the solution A in step (1) was sterilized and filtered with two 0.22 μm polyethersulfone filter elements to obtain intermediate B;

(3) the intermediate B was filled, melt-sealed, and packaged to obtain the product.

EXAMPLE 13

Preparation of the Lyophilized Powder Injection of the Compound of Formula II-1

The composition of the preparation: 10 g of the compound of formula II-1 and 2000 mL of water for injection.

Preparation Process (1) a selected weight of the compound of formula II-1 was added to 70% of a selected volume of water for injection. The mixture was stirred until completely dissolution to obtain solution A;

(2) 30% of the selected volume of water for injection was added to the above solution A. The pH was adjusted to 8.5-9.5 while stirring. The mixture was pre-filtered through a plate-and-frame filter to obtain solution B;

(3) The solution B in step (2) was sterilized and filtered with two 0.22 μm polyethersulfone filter elements to obtain solution C, which was filled and half plugged to obtain intermediate D;

(4) the intermediate D was freeze-dried at a temperature of −40° C. to −50° C. and a pressure of 10 Pa to 22 Pa. The temperature during the freeze-drying process was raised as follows:

(a) the temperature was set at −45° C. to −30° C., and the pre-freezing was carried out for 2.0 h;

(b) the temperature was raised to −30° C. to −20° C., and the sublimation was carried out for 4.0 h;

(c) the temperature was raised to −20° C. to −10° C., and the sublimation was carried out for 1.5 h;

(d) the temperature was raised to −10° C. to 0° C., and the sublimation was carried out for 1.0 h;

(e) the temperature was raised to 0° C. to 15° C., and the sublimation was carried out for 1.5 h; and (f) the temperature was raised to 15° C. to 25° C. and preserved for 2.0 h.

After the heat preservation was completed, it was stoppered, taken out of the box and capped. The lyophilized powder injection of the compound of formula II-1 was thus obtained.

EXAMPLE 14

Comparison of Solubility

The solubility of torsemide, M3, I, I-1, I-2, I-3, I-4, II, II-1, II-2, III, III-1 and III-2 was compared. The results are as follows:

TABLE 2

Comparison of water solubility of compounds

| Sample | API:water | Phenomenon | Conclusion |
|---|---|---|---|
| Torsemide | 3 mg:10 mL | Completely dissolved | Very slightly soluble |
| M3 | 15 mg:10 mL | Completely dissolved | Slightly soluble |
| Compound I | 1.6 g:10 mL | Completely dissolved | Soluble |
| Compound I-1 | 2.1 g:10 mL | Completely dissolved | Soluble |
| Compound I-2 | 2.1 g:10 mL | Completely dissolved | Soluble |
| Compound I-3 | 1.9 g:10 mL | Completely dissolved | Soluble |
| Compound I-4 | 1.9 g:10 mL | Completely dissolved | Soluble |
| Compound II | 1.8 g:10 mL | Completely dissolved | Soluble |
| Compound II-1 | 2.2 g:10 mL | Completely dissolved | Soluble |
| Compound II-2 | 2.0 g:10 mL | Completely dissolved | Soluble |
| Compound III | 1.7 g:10 mL | Completely dissolved | Soluble |
| Compound III-1 | 2.0 g:10 mL | Completely dissolved | Soluble |
| Compound III-2 | 1.9 g:10 mL | Completely dissolved | Soluble |

The solubility experiment results show that the solubility of the pyridine sulfonamide phosphate compound in Examples 1-11 is better than that of torsemide and M3, which has the advantage of high druggability.

EXAMPLE 15

Comparison of Diuretic Effects

Male SD rats (body weight: 180±20 g) were randomly divided into 14 groups with 3 rats in each group. Each rat was administrated 30 mL/kg normal saline through intragastric administration. After intragastric administration of normal saline, except the blank control group, each group was administrated one drug (10 mg/kg, ig, 1 mg/mL, formulation prescription: normal saline dissolution). Urination for 4 h was collected. The results are shown in Table 3:

TABLE 3

Comparison of urine output of different compounds

| Compound | Dosage and administration route | Urine output (mL/kg, 4 h) |
|---|---|---|
| Blank control | — | 19.2 |
| Torsemide | 10 mg/kg, ig | 105.3 |
| M3 | 10 mg/kg, ig | 107.2 |
| Compound I | 10 mg/kg, ig | 121.4 |
| Compound I-1 | 10 mg/kg, ig | 127.6 |
| Compound I-2 | 10 mg/kg, ig | 119.8 |
| Compound I-3 | 10 mg/kg, ig | 123.4 |
| Compound I-4 | 10 mg/kg, ig | 125.6 |
| Compound II | 10 mg/kg, IG | 119.3 |
| Compound II-1 | 10 mg/kg, ig | 131.4 |
| Compound II-2 | 10 mg/kg, ig | 135.2 |
| Compound III | 10 mg/kg, ig | 113.7 |
| Compound III-1 | 10 mg/kg, ig | 123.8 |
| Compound III-2 | 10 mg/kg, ig | 124.5 |

The diuretic effect experiment results show that the diuretic effect of the pyridine sulfonamide phosphate compound in Examples 1-11 is similar to that of torsemide or better than that of torsemide, which has the advantage of high druggability.

All documents mentioned in the present invention are incorporated herein by reference, just as if each document was individually cited as a reference.

What is claimed is:

1. A pyridine sulfonamide phosphate compound of formula I or a pharmaceutical salt thereof:

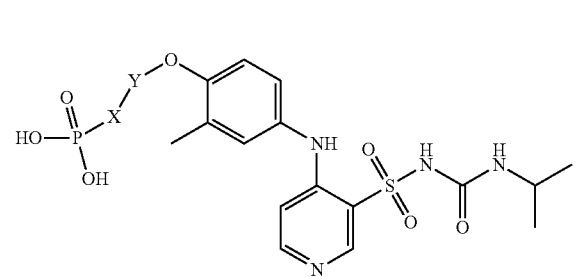

I wherein
X is O or C, or does not exist; and
Y is C, or does not exist;
when X and Y do not exist, O is directly connected to P;
when X exists but Y does not exist, X is directly connected to O; and
when Y exists but X does not exist, Y is directly connected to P.

2. The pyridine sulfonamide phosphate compound or pharmaceutical salt thereof according to claim 1, wherein the pharmaceutical salt includes metal salt, salt formed with inorganic base, salt formed with organic base, and salt formed with basic amino acid.

3. The pyridine sulfonamide phosphate compound or pharmaceutical salt thereof according to claim 2, wherein the metal salt includes alkali metal salt including sodium salt or potassium salt, and alkaline earth metal salt including calcium salt, magnesium salt, barium salt or aluminum salt; and wherein the organic base includes trimethylamine, triethylamine, tripropylamine, tributylamine, or diisopropylethylamine.

4. The pyridine sulfonamide phosphate compound or pharmaceutical salt thereof according to claim 1, being a compound selected from the group below:

| Compound | Structural formula |
|---|---|
| I-1 | (sodium phosphate ester of the parent sulfonylurea pyridine compound, disodium salt) |
| I-2 | (dipotassium phosphate ester analog) |
| I-3 | (phosphoric acid form, triethylamine salt) |
| I-4 | (phosphoric acid form, tributylamine salt) |
| II-1 | (oxymethyl phosphate disodium salt analog) |

| Compound | Structural formula |
|---|---|
| II-2 | 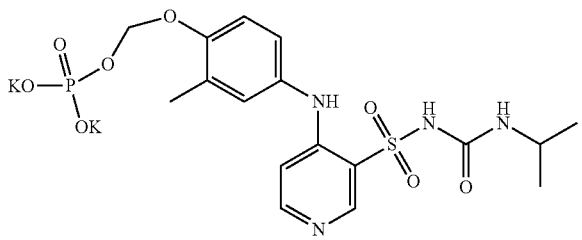 |
| III-1 | 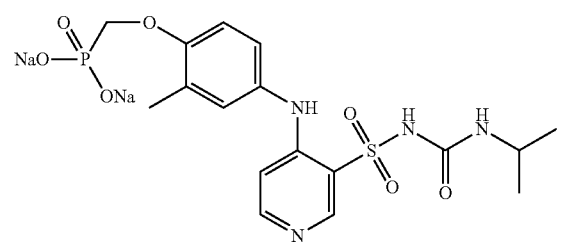 |
| III-2 | 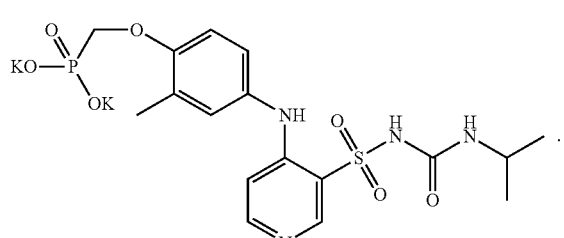 |
5. A method for preparing the pyridine sulfonamide phosphate compound or pharmaceutical salt thereof according to claim 1, comprising the steps of:
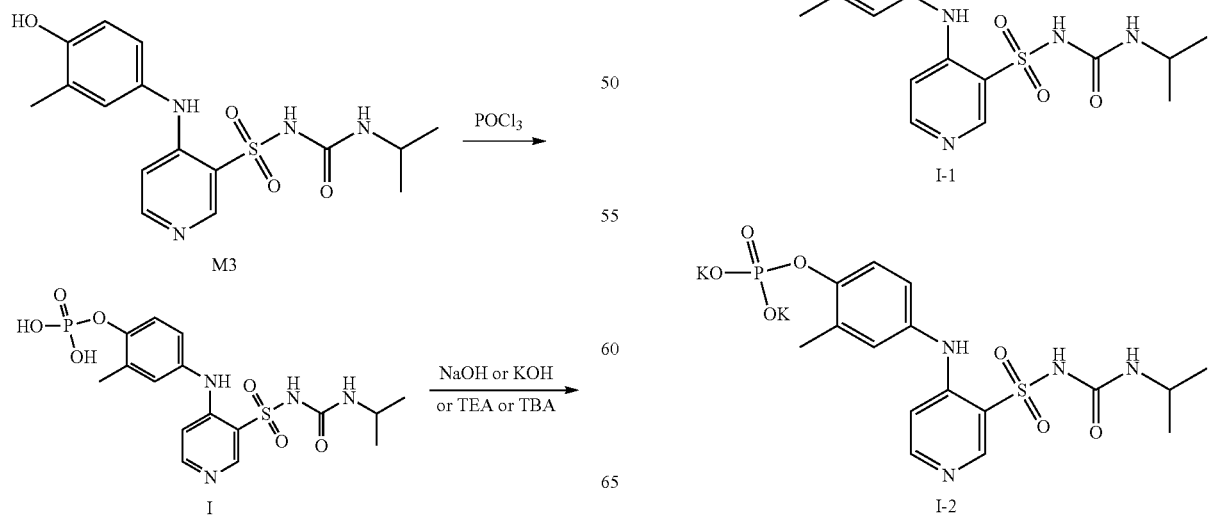

21
-continued

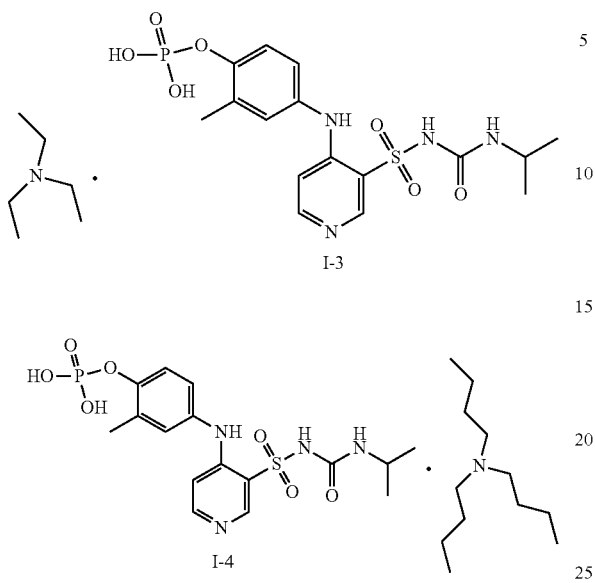

reacting M3 with POCl$_3$ to give the compound of formula I; and reacting the compound of formula I with sodium hydroxide, potassium hydroxide, triethylamine or tributylamine to give compounds of formula I-1, I-2, I-3 and I-4, respectively.

6. A method for preparing the pyridine sulfonamide phosphate compound or pharmaceutical salt thereof according to claim 1, comprising the steps of:

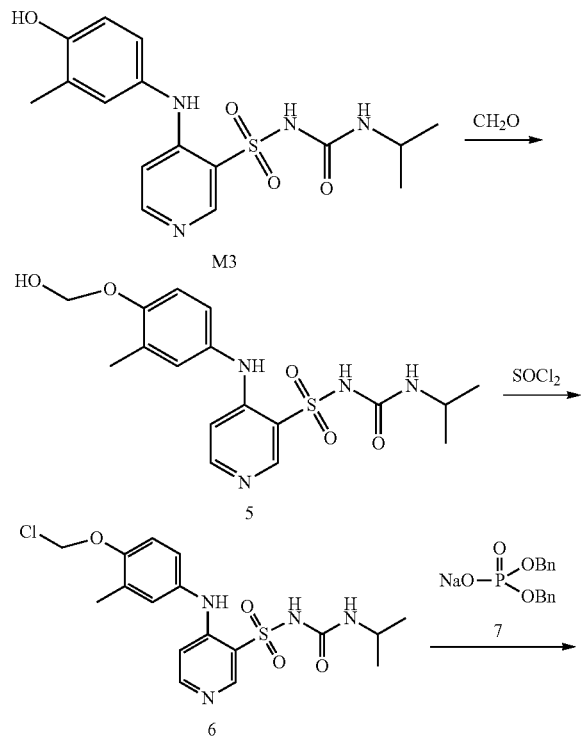

22
-continued

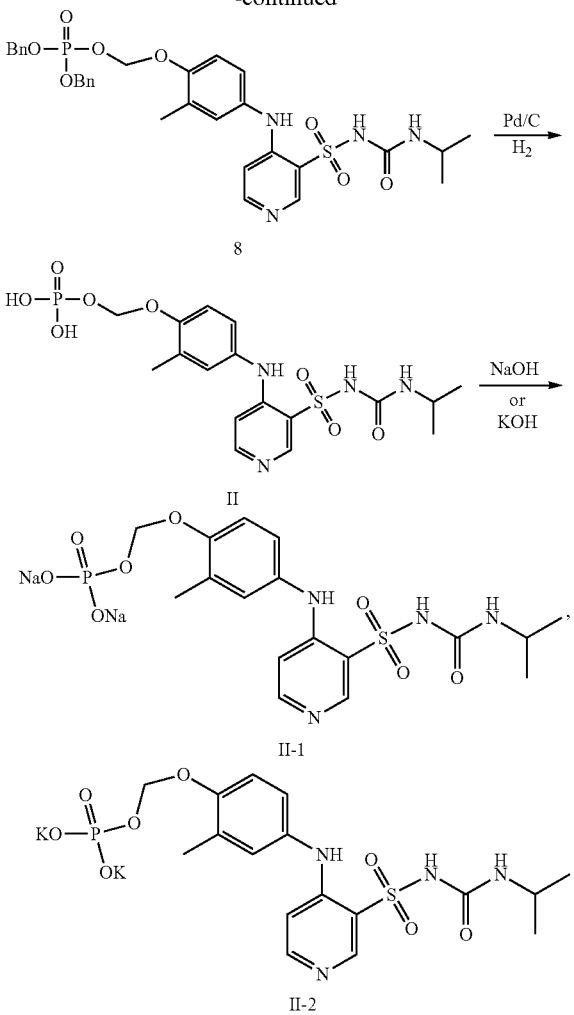

subjecting M3 to hydroxymethylation with paraformaldehyde to give compound 5, subjecting compound 5 to chlorination with thionyl chloride to give compound 6, subjecting compound 6 to esterification with dibenzyl phosphate sodium salt 7 to give compound 8, subjecting compound 8 to debenzylation via hydrogenation with palladium on carbon and hydrogen to give a compound of formula II; and reacting the compound of formula II with sodium hydroxide or potassium hydroxide to give compounds of formula II-1 and II-2, respectively.

7. A method for preparing the pyridine sulfonamide phosphate compound or pharmaceutical salt thereof according to claim 1, comprising the steps of:

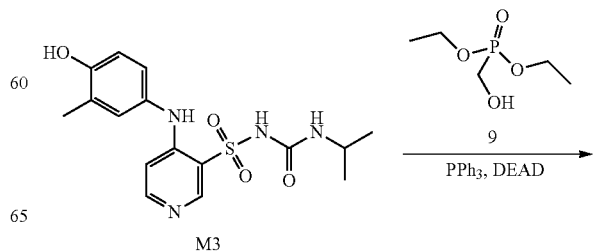

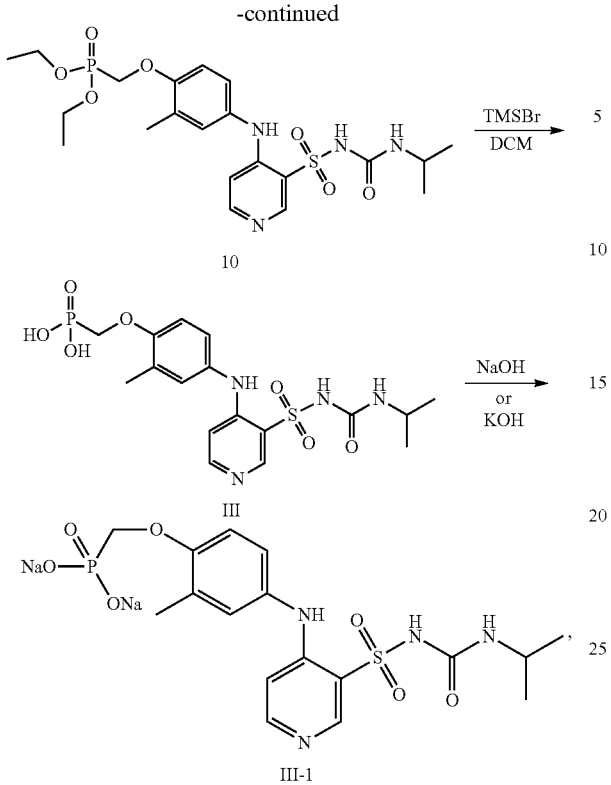

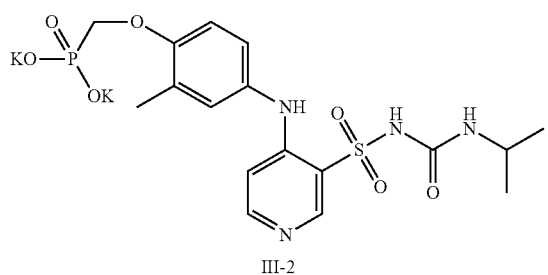

subjecting M3 to esterification with diethyl hydroxymethyl phosphonate (9) to give compound 10, and subjecting compound 10 to deethylation to give a compound of formula III; and reacting the compound of formula III with sodium hydroxide or potassium hydroxide to give compounds of formula III-1 and III-2, respectively.

8. A pharmaceutical composition, comprising a therapeutically effective amount of the pyridine sulfonamide phosphate compound or pharmaceutical salt thereof according to claim 1 and a pharmaceutically acceptable excipient.

* * * * *